United States Patent [19]

Abele et al.

[11] 4,339,799
[45] Jul. 13, 1982

[54] TOMOGRAPHIC SCANNER

[75] Inventors: Manlio G. Abele, Garden City; Norman E. Chase, Yonkers, both of N.Y.; Gareth A. Mair, Stratford, Conn.

[73] Assignee: New York University, New York, N.Y.

[21] Appl. No.: 850,891

[22] Filed: Nov. 15, 1977

[51] Int. Cl.³ .................... G06F 15/42; G01N 21/00
[52] U.S. Cl. ............................. 364/414; 250/445 T; 364/515
[58] Field of Search ............... 364/414, 415, 514–516, 364/559, 565; 250/445 R, 445 T, 336, 362, 363 R, 363 S

[56] References Cited

U.S. PATENT DOCUMENTS

| | | | |
|---|---|---|---|
| 3,924,129 | 12/1975 | Le May | 250/362 |
| 3,936,636 | 2/1976 | Percival | 250/369 |
| 3,976,827 | 8/1976 | Alien et al. | 364/515 |
| 4,029,948 | 6/1977 | Hounsfield | 364/515 |
| 4,029,963 | 6/1977 | Alvarez et al. | 364/515 |
| 4,068,306 | 1/1978 | Chen et al. | 364/515 |
| 4,074,564 | 2/1978 | Anderson | 364/414 |

*Primary Examiner*—Errol A. Krass
*Attorney, Agent, or Firm*—Daniel M. Rosen

[57] ABSTRACT

A method and apparatus for examining relative movement of two masses of different radiation attenuation characteristics, separated by a boundary and moving relative to one another over a repetitive motion cycle. The masses are examined from a plurality of successive angles about a common center of rotation. The object is scanned over each motion cycle from each of these angles to derive a plurality of attenuation coefficients encompassing the entire motion cycle. A plurality of differential points is calculated between adjacent scans of a single motion cycle, and a single composite image of all of these differential points is reconstructed for each individual time period of each motion cycle for display.

12 Claims, 18 Drawing Figures

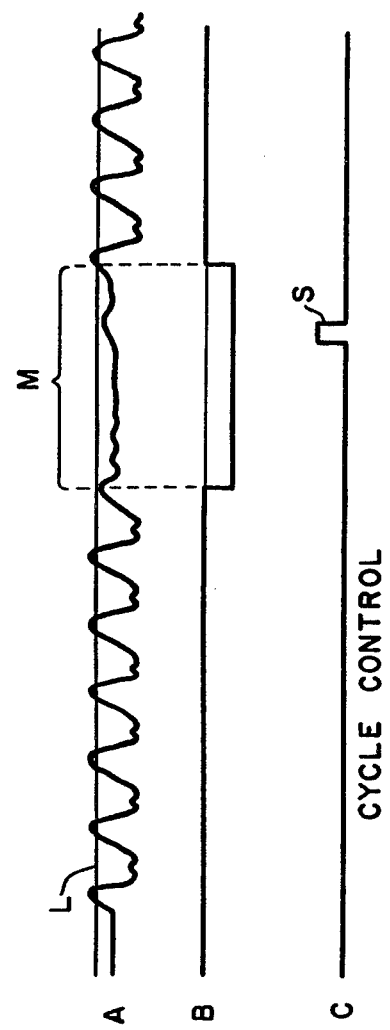

PLOTTING OF $\mu - \langle \mu \rangle$ ACROSS A PLANE INTERFACE BETWEEN UNIFORM MEDIA

TOMOGRAPHIC SCANNER

THE INVENTION

This invention relates generally to the field of radiography, and more particularly to methods and apparatus for obtaining, by radiographic means, an image of a field having the characteristic of varying radiographic attenuation during a scanning process.

Various techniques for radiographic examination of a body plane have been described in the prior art. For example, U.S. Pat. No. 3,778,614 issued Dec. 1, 1973, shows a method of, and apparatus for examining a body by means of a beam which traverses a series of parallel paths across a section of the body plane. A detector moves in synchronism with the beam in order to provide a measure of the attenuation of the beam along each parallel path through the body plane. At the completion of the scans of the body plane, the beam and detector are orbited about an axis normal to the body plane to a second position and the entire process repeated. After completion of all of the angular rotations necessary through the plane of the section being scanned, all of the various attenuations detected are processed in a series of successive approximations in order to provide a complete set of attenuation coefficients for each body point within the plane. Since attenuation coefficients will vary in accordance with the attenuation of the substance being traversed by the beam, the ultimate image can be displayed as a range of gray scale values representing information concerning the area being scanned. In the human body, attenuation coefficients will vary for normal body tissues, tumors, fat, bone, blood and other typical or atypical materials found during such scan of the human body. This technique has been found particularly useful for identification of various brain diseases and abnormalities, and involves a relatively minor amount of the patient discomfort otherwise associated with other types of radiographic techniques such as pneumography, angiography and radioactive isotope scanning. In more recent developments, shorter examination time has been achieved with an apparatus such as is described in U.S. Pat. No. 3,999,073. In that patent attenuation data signals are derived by directing a fan-shaped beam of radiation emanating from a source through the body in the plane to be examined, and providing a band of detectors on the other side of the body which will measure the radiation transmitted along a set of beam paths across the fan. Since the beam paths now simultaneously traverse the entire area being examined, a series of parallel paths such as described in the aforementioned prior art patent is no longer necessary. In the latter case, the fan-shaped beam subtends an angle sufficient to include the entire region of interest in the plane of the body so that complete scan of the plane can be made merely by orbiting the source and detectors around the body at different angular positions to accumulate the necessary data.

An even further modification of the foregoing technique employs variations in the manner in which data is collected and is described in copending application Ser. No. 635,165 filed Nov. 25, 1975, and now abandoned, assigned to the assignee of the present invention.

The operation of all the foregoing systems result in a series of attenuation coefficients derived from measurements made through various angles of a single body plane. Since rotational or orbital positioning is necessary in all of the foregoing techniques for completing the image, it will be evident that the total time necessary for creating a single image will encompass the time needed for making at least one complete orbital scan. Since the area of interest normally employed in devices of this type include segments of the human body, it will be apparent that the size and content of the rotating machinery employed in the situation imposes a limit on the rotational speed that can be achieved. In deriving attenuation coefficients by measuring the attenuation characteristics of certain organs which exhibit normal movement, such as the heart, it will be apparent that a single orbiting scan will not provide sufficient information within the framework of the known prior art technology as described above in order to provide meaningful data for the reconstruction of an image. This is particularly true when the movement of the mass within the area of interest changes the amount of attenuated radiation occurring during the scanning interval.

It is therefore the principal object of the present invention to provide a method and apparatus for measuring and indicating the change in attenuation of an area under examination during the scanning interval.

It is also evident that the examination of the organ which undergoes large scale movements during the examination interval will result in erroneous data readings. Several techniques have been proposed to compensate for the large scale motion of area movement during the scanning interval. For example, in U.S. Pat. No. 3,952,201 issued Apr. 20, 1976, a radiographic apparatus is described wherein a monitoring device is coupled to the organ of interest. During large scale movement of the organ of interest, the monitor indicates to the computer that the organ is no longer within the field of the x-ray device and means are provided for turning off the x-ray source. Since this may result in insufficient data to provide a complete image, the x-ray source is allowed to rotate again in order to provide additional data. Should the monitoring device again indicate a movement of an organ requiring a data shut-off, the source is again turned off and subsequent motion cycles continue until sufficient data has been obtained to complete the image. The difficulty with the foregoing technique is that additional motion cycles are necessary during a relatively slow scanning process in order to complete a single frame picture. In addition, the foregoing technique does not take into account smaller movements of the organ which may desirably be observed and displayed while discriminating against larger scale movements of the organ which will result in a data shut-off.

It is therefore another object of the present invention to provide a compensation technique which will allow for display of small scale movement of an area of interest during the scanning interval, while discriminating against large scale movements which inhibit the accuracy of scanned data.

The foregoing objects are achieved by examination, employing penetrating radiation, of a planar cross-section of two masses of different radiation attenuation characteristics, separated by a boundary, and moving relative to one another over a repetitive motion cycle. The masses are examined from a plurality of successive angles about a common center of rotation. The object is scanned over each motion cycle from each of these angles to derive a plurality of attenuation coefficients encompassing the entire cycle. A plurality of differential points is calculated between adjacent scans of a single motion cycle, and a single composite image of all of these differential points is reconstructed from each individual time period of each cycle for display. In further detail, at the beginning of the first point in the repetitive motion cycle, the average attenuation of the entire planar cross-section of the area to be examined is determined along a first angular position relative to the area. This is accomplished over the entire repetitive motion cycle by sequentially detecting the attenuation over a plurality of equal time intervals of a plurality of segments of the area. Next, a series of differential signals is generated representing the change in average attenuation of adjacent segments within the area per unit time. The unit of time represents time from one of the time intervals to the next of the time intervals over the entire repetitive motion cycle. The foregoing detecting and generating steps are repeated beginning each time at the same first point in successive ones of the motion cycles in the repetitive motion cycle, from each of a plurality of further angular positions, over a single revolution, thereby generating a plurality of further corresponding differential signals representative of attenuation changes per unit of time from each of the plurality of further angular positions to the area being examined. The resulting plurality of differential signals is then correlated into corresponding time locations over one composite motion cycle of the total number of examined repetitive motion cycles, this correlation providing a set of differential signals for each time position in the repetitive motion cycle. Thus, the rate and direction of relative motion of the masses to each other during the motion cycle is derived. This derived signal sequence may be then displayed or otherwise presented in usable form. By using a monitor in conjunction with the object being examined, gross movement may be detected and the data during the gross movement inhibited or otherwise not used in the calculation of the differential signals. Since many differential points are calculated, loss of a certain amount of this data may be tolerated without the need for repeating the motion cycle. If an excessive amount of data is lost, means may be provided for repeating the motion cycle so that the lost data may be recovered.

It should be noted that the foregoing technique is achieved with conventional technology by reconstruction of the entire body plane scanned. However, since the technique of this invention is concerned only with a specific organ, such as the heart, it may be convenient to limit the scan to only that area including and immediately surrounding the region of interest. The derivation and application of a method for scanning and reconstruction of a partial region of interest within a scanned plane is fully described in Applicant's copending application Ser. No. 635,165, filed on Nov. 25, 1975, and assigned to the assignee of the present invention, the disclosure of which is incorporated herein by reference. As is shown in the aforementioned copending application, it is possible to mathematically define a solution for the local value of an attenuation coefficient within a prescribed circle. By using a differential-like approach in the image construction, it is possible to confine both scanning and computation to an area of body scan represented by the prescribed circle.

In reconstruction, the only difference between a partial and a total scanning and reconstruction is in the magnitude and requirements for information storage, speed and interpretation of the results. Thus, the same total reconstruction code for reconstructing a solution can be used for solving the partial reconstruction, the sole specification being the addition of a value defining the prescribed circle of interest. The reconstruction code would proceed with calculation and storage of weighting functions, confined to the circle of interest, back projection and image display. The image display provides the desired value and may be displayed by assigning a grey scale to the range of values, and an image size to each coordinate point to produce a photographic analogous image.

The foregoing brief description of the present invention as well as further objects, advantages, and features will become more apparent following a more detailed description of the preferred embodiments of this invention taken in conjunction with the accompanying drawings, wherein:

FIG. 5 is a timing diagram of the object movement and recycle relationship, and FIGS. 6A & B are symbolic relationships employed herein.

Figure 1:
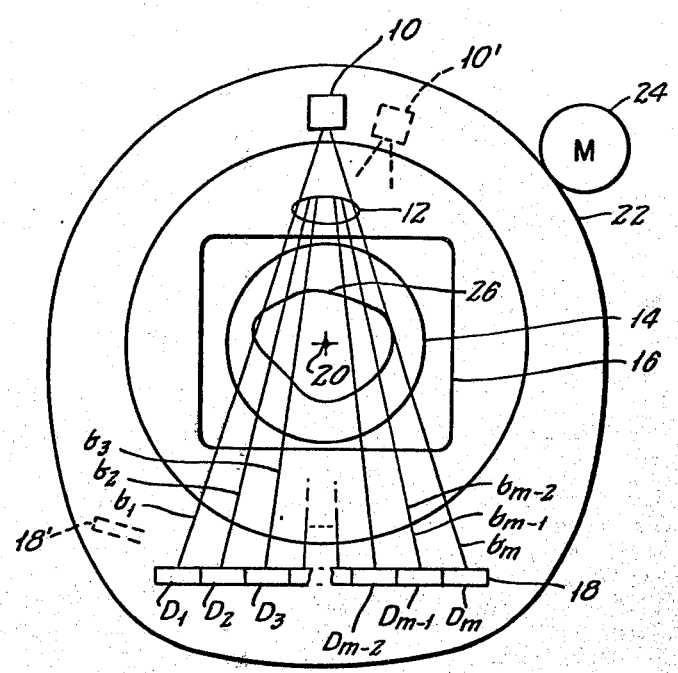
FIG. 1 illustrates a scanning mechanism irradiation mechanism.

Referring now to FIG. 1, a typical construction is illustrated for purposes of radiographic examination of a transverse plane, commonly termed transverse axial tomography. In this embodiment radiation is provided from a source 10, which may be construed as a point source, and which forms a fan-shaped beam 12. The transverse plane 14 to be examined lies within the framework 16 and is supported by suitable means not shown. In typical usage, the framework 16 will be employed to support the body of a human patient and therefore must be suitably sized and shaped in accordance with known devices of this type to accommodate the patient. A supported detection device 18 responds to incident radiation for producing an appropriate output. In preferred form, the detection means 18 consists of a plurality of individual detectors, $D_1, D_2 \ldots D_n$, each of which may be a scintillator and photomultiplier, and including a collimator for confining the radiation reaching each detector to a plane section normal to the axis of rotation which is symbolically indicated as 20.

The source 10 and detection device 18 are secured, in opposition, to a rotatable frame 22 which is preferably annular and which is, in turn, driven by an appropriate motor 24, either by means of direct drive or by means of pulleys, gears or the like. Any conventional technique may be employed for driving the source 10 and detection device 18 with an orbital motion about the axis of rotation 20 and have been described in the prior art. The orbital motion allows the beam 12 to penetrate the transverse plane over a plurality of angular positions.

Located within the transverse plane of area 14 under examination is an examination object 26. The examination object lies in its entirety within the fan-shaped beam 12 so that it may be entirely scanned from a single angular position of the source 10. Although it will be understood that the present invention may be employed with various objects employing repetitive motion cycles, for purposes of illustration it is assumed that the examination object 26 is a human heart and the transverse body plane 14 represents, by its exterior perimeter, the human body. It is not necessary for the examination object 26 to lie exactly over the axis of rotation 20, however, it is essential for the fan-shaped beam embodiment of the present invention that the divergence of the fan-shaped beam 12 encompass at each angular position of the source 10 the entire region being examined. Thus, the width of fan beam 12 is shown as encompassing the entire width of the examination object 26; although using partial reconstruction, the beam need encompass only the area of interest.

The transverse plane 14 defines two masses of different radiation absorption characteristics. In the example of the human heart, the entire interior of the object 26 is filled with blood. In the space surrounding the examination object but within the perimeter of the transverse plane section 14 there is a conglomerate of tissue, bone and other body material, all amounting to a different radiation absorption characteristic. Thus, the examination object 26 will undergo a repetitive motion cycle wherein it will expand with material having a different radiation absorption characteristic than the material surrounding the examination object 26. The path of a single collimated beam within the fan-shaped beam 12 such as, for example, the beam designated $b_1$, passes through a total volume of radiation attenuating material consisting of a first block of attenuating material, external to the object being examined but within the perimeter of the transverse plane 14, and a second block of radiation attenuating material within the examination object 26. The same may be stated for each of the successive beams, $b_2$, $b_3$ . . . $b_n$. From a singular angular position, the entire object 26 is scanned, from $b_1$ detector position through the $b_n$ detector position over one entire repetitive motion cycle of the examination object. In the heart example, the heart is assumed to have a repetition rate of approximately one beat per second. It is then desirable to scan the entire heart represented by the object 26 from positions $b_1$ through $b_n$ over the entire cycle represented by a single heartbeat. It should be noted that attenuation of the x-ray beam generated by the source 10 as it passes through the transverse plane 14 is deduced from the transmissivity along each path and a knowledge of the initial intensity of the beam or ray entering each path. This may be effected by conventional techniques such as is described in the aforementioned copending application, and used in the Tomoscan® 200, manufactured by Philips Medical Systems, Inc. of Shelton, Conn. Thus, the attenuation of any path b will be proportional to the ratio of the beam intensity at the entrance to the transverse plane and the beam intensity at the exit from the transverse plane. By logarithmically converting this ratio, a linear output is obtained so that the total attenuation along the path is equal to the sum of a hypothetical series of elements which define the path itself. As will be evident in the above-cited prior art developments, attenuations for each individual element may be employed to recreate a complete reconstruction of the entire image plane as it is penetrated by the radiation from the source. However, although calculation of the absorptions of individual elements is not necessary for the differential examining method which is employed within the concept of the present invention as will be evident from the following detailed description, certain calculations can be made to insure that objects outside the circle of interest will be ignored, and edge contrasts increased inside the circle of interest.

As shown in FIG. 1, a complete fan-shaped radiation beam encompassing the entire object to be examined from a single angular position illustrated by the solid line describing the source 10 is made along one entire repetitive motion cycle of the object 26. In the example of a human heart, it may be presumed for purposes of discussion that the heart undergoes an average beat time of one second. If it is desired to divide the heartbeat into 100 time periods, then a series of attenuation readings, each covering an average time of 10 milliseconds for each collimated beam path, may be made. Each time period reading will begin at a fixed point in the repetitive motion cycle so that all readings may be time identifiable. This may be accomplished with a standard electrocardiograph monitoring circuit, with readings beginning a fixed time after the end of a definable point, such as the QRS complex. With an average data sampling time of 10 milliseconds per path, 100 data readings may be taken during each repetitive motion cycle, for a series of 100 repetitive motion cycles, to present data sufficient for 100 reconstruction segments used to make up one entire composite repetitive motion cycle.

In preferred form with regard to FIG. 1, the detection device 18 includes 30 detectors encompassing the entire object. A first read sequence is taken between the zero and 1 degree angular positions of the source 10. The scanning system may thus be designed to take 30 readings during a period of, for example, one millisecond. The rotating frame 22 is moving at a constant rate around the framework 16 by action of the motor drive 24, such that, for example, the source 10 will move from an angular position of 0° with respect to a predetermined radial line reference relative to the center of rotation 20 to an angular position of 1°, position 10', in one second. During this one second time, the motion cycle period is divided into 100 time slots, $t_1$, $t_2$ . . . $t_{100}$ of 10 milliseconds each. For purposes of calculation, during each 10 millisecond time slot, 10 separate readings are taken from each individual detector. The readings from each detector are averaged together to produce a separate average attenuation reading from each path for each 10 millisecond period during the time that source 10 moves from the 0° to 1°. Clearly, a larger or lesser number of readings per detector could be used, but 10 appear to be optimal for scanning a human heart. At the end of the 1° position the source 10 will be at position 10' and the detector 18 will be at position 18'. The entire read sequence is then repeated from the one to two degree position, and so on around the entire object. Thus, for each degree position, 100 time slot readings over each motion cycle are taken.

Figure 2:
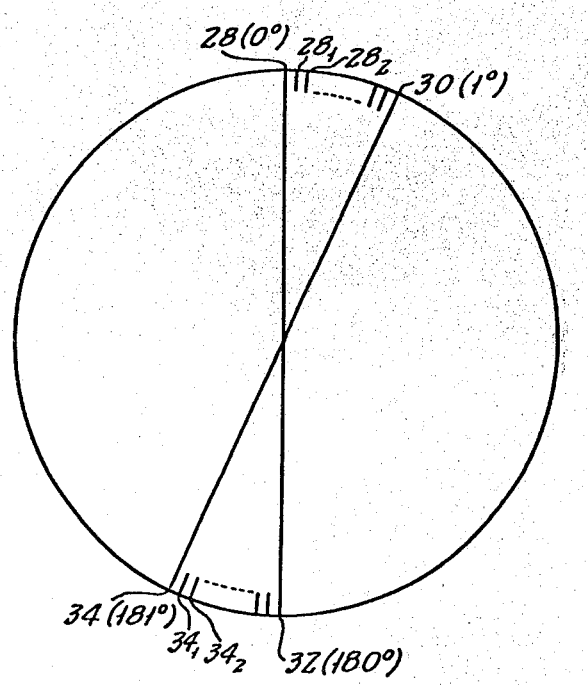
FIG. 2 is an illustration of the cycling mode employed in the present invention.

Referring to FIG. 2, the schematic illustration of the motion cycle coverage of the device of FIG. 1 is explained. Thus, the 0° position is represented by the first radial line 28 and the 1° position (in exaggerated form) is represented by the second radial line 30. As was explained above, at the end of the period of time that it takes for the source to move from position 10 to position 10' at FIG. 1, shown respectively as the first radial line 28 and the second radial line 30, a time period of one second has transpired. On an extrapolation basis it should be noted, for this example, that the entire rotating frame or ring 22, at a degree per second movement, will take 360 seconds or six minutes to make one entire revolution. During the time period encompassed by one second, a series of 1,000 readings per path have been taken, 10 each from a single detector being averaged over a period of 10 milliseconds, to result in 100 sampling signals per path. These 100 sampling signals represent one entire repetitive motion cycle of the heart or object 26 under scan. Thus, an average attenuation reading is available for each of the 100 time sequential positions over the 1° interval from 28 to 30. The same information is repetitively available, as the sequence continues around the entire circle as shown in FIG. 2 including, for example, the 180° position defined by radial line 32 and the 181° position defined by radial line 34. Again, between positions 32 and 34 100 time sequential average attenuation readings are taken over an entire single repetitive motion cycle. It is evident that attenuation readings can be taken at a fixed point in each successive repetitive motion cycle, over successive angular positions, until the entire object has been completely encircled by the rotatable frame 22 completing a single revolution.

It now remains only to provide differential signals from the collected data in order to reconstruct differential positions representing the rate of change of movement of the object over the period of time of analysis. By way of example, if position 28' (FIG. 2) represents the 200 millisecond time point position after initiation of a repetitive motion cycle, out of 100 points of reading, and position 32' similarly represents an interval of 200 milliseconds after the initiation of a repetitive motion cycle, but at a later angular position (between 180° and 181°) and since this is repeated for the entire range between 0° and 360°, then it is evident that attenuation data will be available for repetitive motion cycles at all the various angular positions encompassing one entire revolution of the object. For calculating differentials, it is only necessary to subtract the average attenuation of adjacent successive beam time slot positions ($t_n - t_{n-1}$) within a single repetitive motion cycle for creating a series of differential attenuation values representing the rate of change over a given unit of time. For example, for calculation, in the first degree position between lines 28 and 30, of the differential attenuation rate $d\beta/dt$ between the positions representing 0.50° and 0.49°, it is necessary only to subtract the attenuation data at the higher angular position from the attenuation data at the lower angular position and divide by the fixed interval of time between the successive samplings. Within the framework of the present time description, the angular position at 0.50° may be calculated as follows: $d\beta/dt = (\beta 0.50° - \beta 0.49°)/\Delta t$.

Since the time intervals in the above-identified case are conducted over 10 millisecond durations, the time differential $\Delta t$ for calculation of the differential attenuation would represent the 10 millisecond interval. Thus, for example, at 500 milliseconds, $d\beta/dt$ is available at 0.5°, 1.5°, 2.5°, ... 359.5°. Similarly, at 750 milliseconds, $d\beta/dt$ is available at 0.75°, 1.75°, 2.75°, ... 359.75°. Therefore, $d\beta/dt$ is available in all cycles, from 10 milliseconds to 1,000 milliseconds, at intervals of $\Delta\theta$, where $\Delta\theta$ equals 0.01° from 0° all the way through 359.99°. Stated in another way, 100 $d\beta/dt$ positions are definable at all angular positions beginning at 0° plus $\Delta\theta$, 1° plus $\Delta\theta$, 2° plus $\Delta\theta$, etc., through 359° plus $\Delta\theta$. Thus, with a resolution of 0.01° the entire object is scanned and divided into 100 time displaced segments. For completion of the reconstructed image, it is now only necessary to reconstruct all of the differential signals by correlating the plurality of differential signals into their corresponding time locations to result in a series of differential images of successive time positions to show one single composite motion cycle of the total number of examined repetitive motion cycles. The correlation will provide a set of differential signals for each time position in the repetitive motion cycle, thereby indicating the rate and direction of relative motion of the two masses relative to one another being scanned. It should be noted that the differential positions can be reconstructed in accordance with their mathematical representation to indicate whether the object is expanding or contracting. In accordance with the differential formula set out above, an expanding object will give rise to a positive differential whereas a contracting object will give rise to a negative differential. In conventional display formats, such as CRT or printers, the positive differential can be provided as a white spot and a negative differential as a black spot.

Figure 3A:
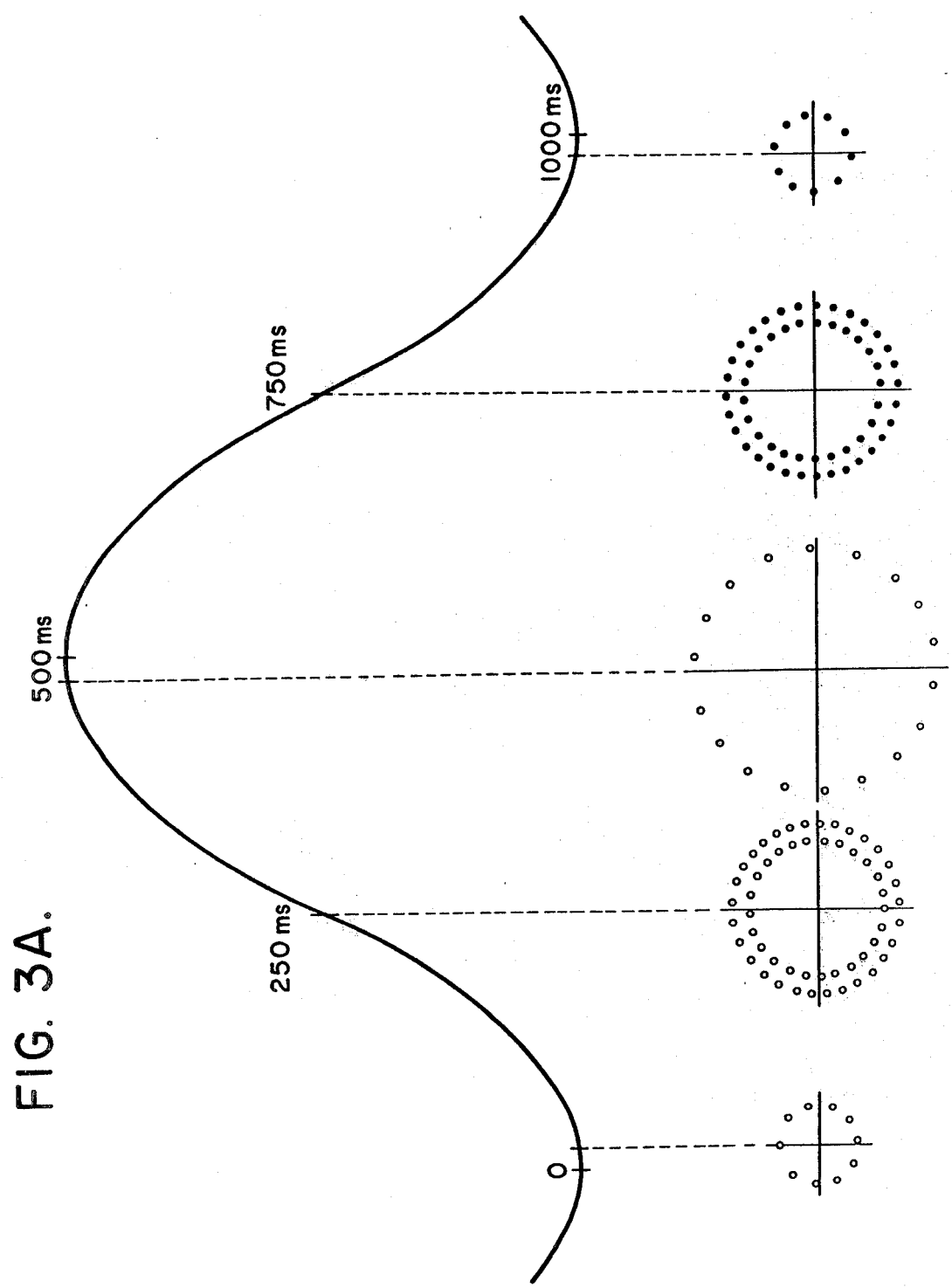
FIGS. 3A–K is a timing diagram of the position of a moving object and its differential images.
Figure 3B:
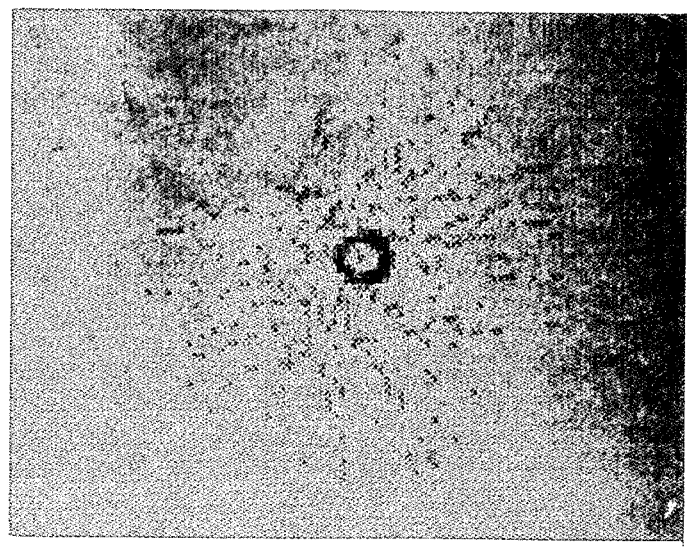
Figure 3C:
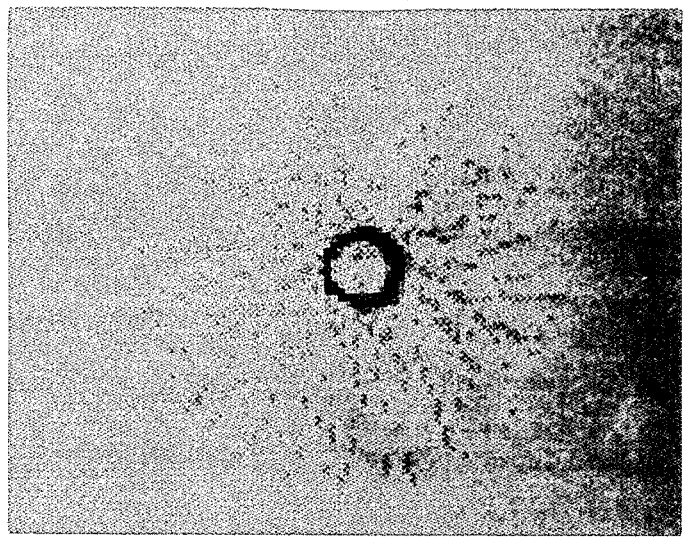
Figure 3D:
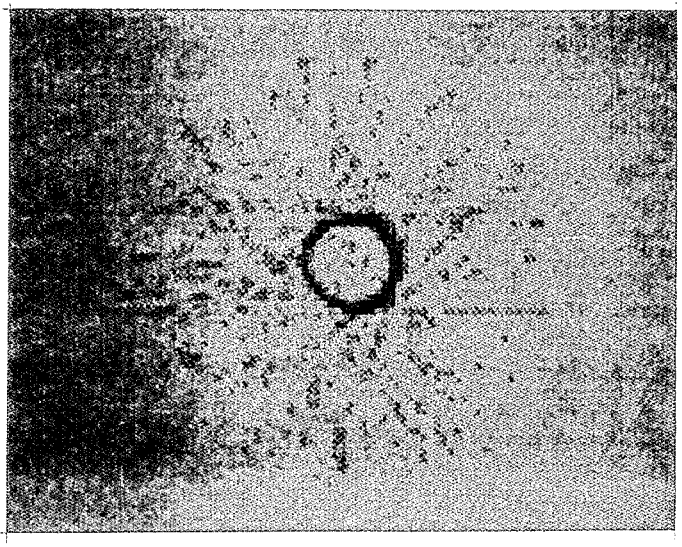
Figure 3E:
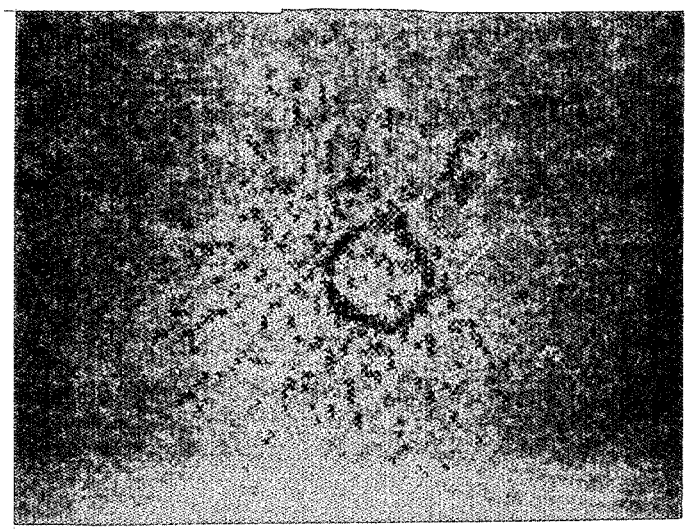
Figure 3F:
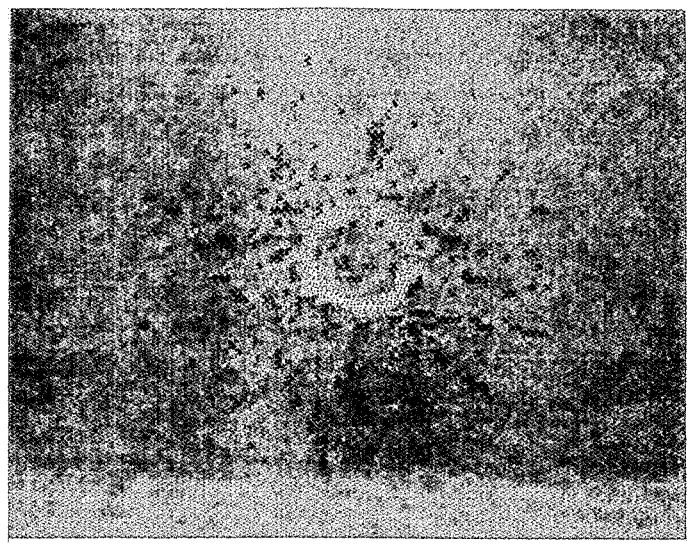
Figure 3G:
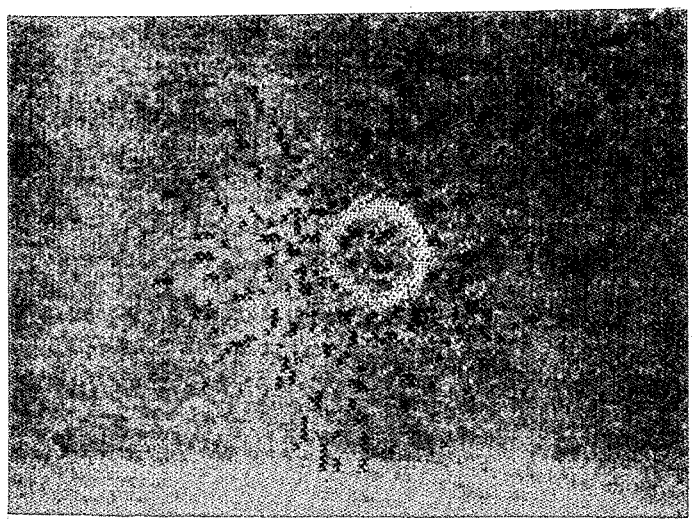
Figure 3H:
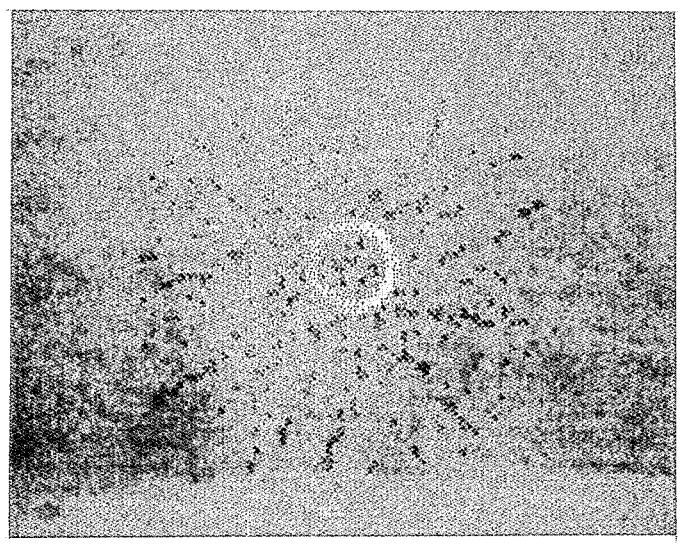
Figure 3I:
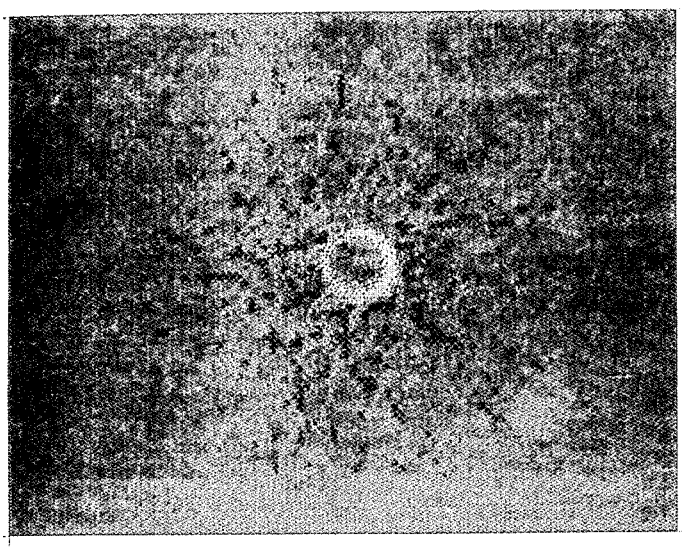
Figure 3J:
Figure 3K:
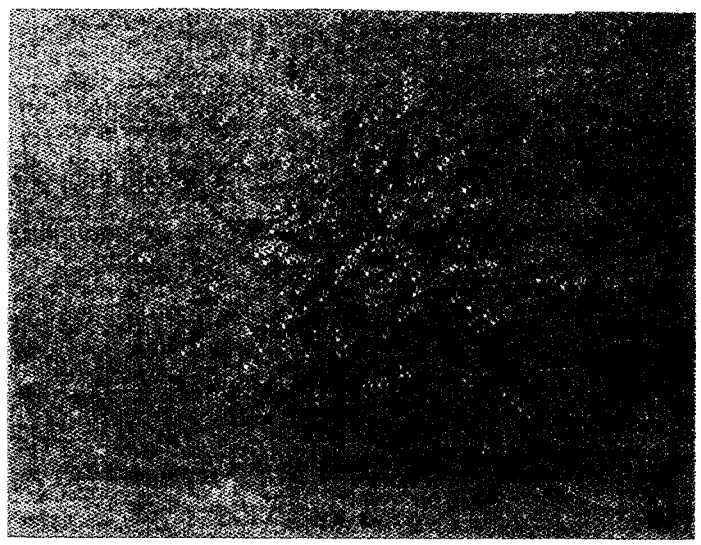

With reference to FIG. 3A, the movement of a varying image in accordance with the sine wave distribution may be demonstrated. Thus, the curve of FIG. 3 represents a sinusoidal wave form illustrating the approximate rate of change or motion of a repetitively motion cycling object such as a heart. Thus, with reference to the first time position of the sinusoidal cycle, representing 0 plus $\Delta\theta$, where $\Delta\theta = 0.01°$, the object is assumed to be at its most contracted and beginning its expansion. Thus, since there is minimum rate of change at this point, the differential reconstruction shown in the corresponding image for this point shows a distribution around a central axis of extremely few distribution points since most of the differential calculations for the individual adjacent paths will show a zero or negligible rate of change. At the 250 millisecond position, the object will be undergoing its greatest rate of change in an ascending direction. Thus, the corresponding reconstruction image will show a dense distribution of white spots, it being understood that the color will be the convention for ascending or increasing positive differentials. At the 500 millisecond position, the heart has reached its largest expansion and again is undergoing its slowest rate of change at this point. Accordingly, the corresponding reconstruction will again show a thinly dispersed series of differential points. At the 750 millisecond position, the object will be undergoing its most rapid rate of change in a descending or contracting phase. Accordingly, all the differentials will not be calculated as negative values and a dense distribution of black spots, of corresponding diameter, will be evident in a display. At the 1,000 $\Delta\theta$ millisecond position, the image reconstructed will be precisely that as was originally shown for the first position. A comparison of the density magnitude of differential points with the original wave form illustrates the phase shift of 90° anticipated and confirms that a differential has been achieved.

For purposes of illustration, with reference to FIGS. 3B-3K, a simulation or phantom was imaged in accordance with the techniques described above. The phantom was a cylindrically-shaped balloon, pulsed from contraction to full expansion and back to full contraction, over a one minute period. A series of 10 images was taken along a plane normal to the long axis of the phantom at intervals of six seconds, and provided the sequence of illustration shown as FIGS. 3B-3K. The expansion and contraction rates are clearly evident as a corresponding density or grey scale value of white (expansion) and black (contraction) points. The imaging was accomplished using a Tomoscan ® 200, available from Philips Medical Systems, Inc., Shelton, Conn.

All of the foregoing has been described in conjunction with a fan-shaped beam. However, it will be evident that any of the methods or techniques employed for radiographic examinations such as were described earlier may be employed in conjunction with the techniques of the present invention. For examining one particular area of interest, the fan-shaped or divergent beam with a divergence sufficient to encompass the organ of interest may be preferable. In addition, although a rotation rate of 1° per second has been described, it will be apparent that any speed or combination of speeds may be employed in accordance with the techniques of the present invention. In addition, although only one revolution has been described, additional revolutions may also be employed although the limitations of data storage capacity would indicate that data should not be duplicated on subsequent revolutions.

It should be noted that the foregoing technique is described with conventional technology by scanning reconstruction of an entire body plane scanned. However, since the technique of this invention is concerned only with a specific organ, such as the heart, it may be convenient to limit the scan to only that area including and immediately surrounding the region of interest. The derivation and application of a method for scanning and reconstruction of a partial region of interest within a scanned plane is fully described in Applicant's copending application Ser. No. 635,165, filed on Nov. 25, 1975, and now abandoned and assigned to the assignee of the present invention; the disclosure of which is incorporated herein by reference, and in the continuation-in-part of said copending application, filed on the same date as this application and granted Ser. No. 850,892, the disclosure of which is also incorporated by reference herein. As was noted previously, and shown in the aforementioned copending application, it is possible to mathematically define a solution for the local value of an attenuation coefficient within a prescribed circle and thus to reduce the effect of attenuation due to objects outside of the circle. By using a differential-like approach in the image reconstruction, it is possible to confine both scanning and computation to an area of body scan represented by the prescribed circle.

Figure 6A:
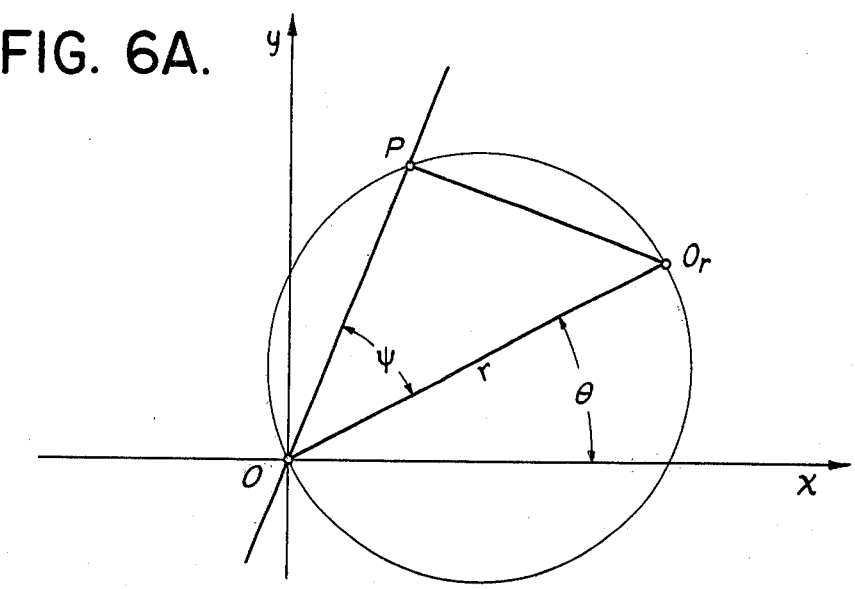

In polar coordinates, generally defined in FIG. 6A, and as derived more completely in the aforementioned copending and continuation-in-part applications, the differential attenuation coefficients are calculated in accordance with the relationship $$\Delta\mu = (\mu - <\mu>)_{r,\theta} = \frac{1}{4\pi r_1} \int_0^\pi g\,[|r\cos(\psi - \theta)|,\psi]\,d\psi \quad (1)$$

where g is a weighted attenuation factor calculated as function of the attenuation coefficients and radius of the prescribed circle of interest.

An important property of equation (1) is the uniform averaging property of the attenuation measurement over each concentric circle of the image reconstruction sequence, as a result of the integration over $2\pi$. Thus, the effect of the statistical fluctuations of the individual measurements of $\beta$ is minimized uniformly over the entire reconstruction area.

Figure 6B:
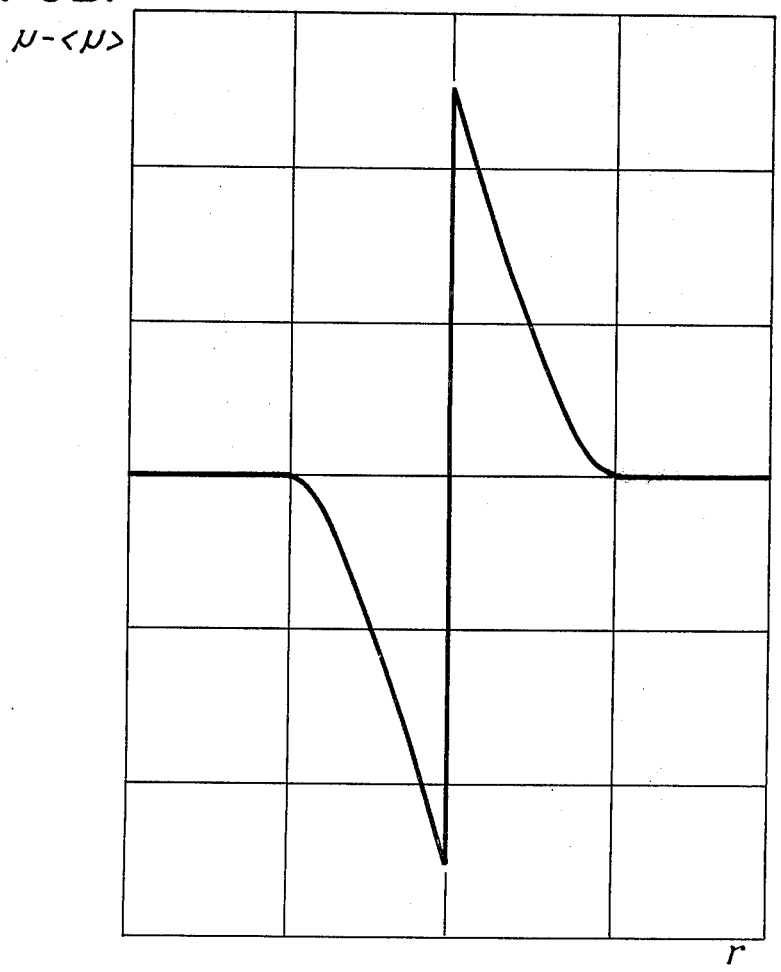

One advantage of confining the scanning to a limited region is that the x-ray beam flux density can be increased in the region of localized scanning and reconstruction without increasing the overall exposure of the surrounding tissues of the body section. Thus, improved spatial resolution and lower noise level can be achieved in the partial image reconstruction. For very small values of the prescribed circle, the equation (1) acquires the essential property of a local average of the second derivative of $\mu$. This is illustrated in FIG. 6B where the value of $\mu - <\mu>$ is plotted versus the distance from a plane interface between two uniform media. Thus, in a general situation of image reconstruction across sharp boundaries, between media of different physical properties, the boundary would be described by one of the family of equations:

$$\mu - <\mu> = 0$$

provided that the radius of the averaging circle is smaller than the local radius of curvature of the interface in the scanning plane.

In reconstruction, the only difference between a partial scanning and reconstruction and a total scanning and reconstruction is in the magnitude and requirements for information storage, speed and interpretation of the results. Thus, the same total reconstruction code for reconstructing a solution for $\mu$ can be used for solving the partial reconstruction with the sole specification of the value "l" defining the circle of interest. The reconstruction proceeds with calculation and storage of weighting functions, confined to the prescribed circle where the limited radius is taken into account, back projection and image display. The image display provides the value $\mu - <\mu>$ and may be displayed by assigning a signed line grey scale to the range of values of $\mu$ or $\mu - <\mu>$ and a pixel size to each coordinate point (x,y in cartesian or $r\cos\theta$, $r\sin\theta$, in polar coordinates) to produce a photographic analogous image. Other techniques for display may obviously be employed as are conventional.

It will thus be evident that the imaging is accomplished for purposes of displaying the motion of a boundary by determining the value and direction, or sign, of the velocity of corresponding points on the boundary, and assigning values to the points on a line grey scale corresponding to those values and directions, or signs.

The foregoing technique therefore provides an abundance of differential points for the reconstruction of each image. In fact, sufficient information is available during the course of a single revolution of the source that a portion of the information derived during the course of a revolution may be discarded without seriously affecting the informational content of the total composite reconstruction. This factor may be taken into account and be of advantage when it is realized that the heart is positioned physiologically in a manner such that large scale movements may move it outside the area of the fan beam, thereby destroying the accuracy of the readings. It may be observed with the amount of data points provided that even large scale movements of the heart, caused by breathing of the patient or otherwise resulting from patient movement during the course of the scan may conveniently be ignored without seriously affecting the quality of an entire composite image resulting from a single revolution. Detection of the movement of the organ is possible by several methods. For example, a chest probe monitor can be provided with appropriate level detection circuitry in order to indicate that the heart has moved sufficiently from its desired position so as to seriously affect the quality of the data being scanned. In such case, the monitor may be adapted to turn off the flow of data or otherwise instruct the computer to ignore the data until the heart has moved back into its appropriate location. A limit as to the amount of data which may be turned off during a single motion cycle can be imposed into the system during the reading so that, should sufficient quantity of data be missing from the total data obtained in a single revolution, the revolution may be repeated. Other means are possible for determining movement of the heart, and a chest probe is only one example for this function.

With respect to the use of monitoring devices to determine organ movement for the purpose of discontinuing erroneous data readings, it will be evident that the technique of the present invention will provide a series of attenuation readings over a plurality of paths over a complete repetitive motion cycle which will be in a relatively narrow range resulting from the normal movement of the organ. Taking this into account, compensation for gross organ movement may be realized by placing appropriate level detection about the ranges of interest normally expected from the attenuation data received during an entire cycle of movement. Should the attenuation data exceed the ranges of interest by a defined margin, the scanning devices can be instructed to ignore data received during the margin excesses. This can be accomplished by means of specific apparatus or by employing computer programming techniques which will recognize the exceeding of defined limitations and instruct the storage devices not to take into account data scanned during the period of the margin excesses.

Figure 4:
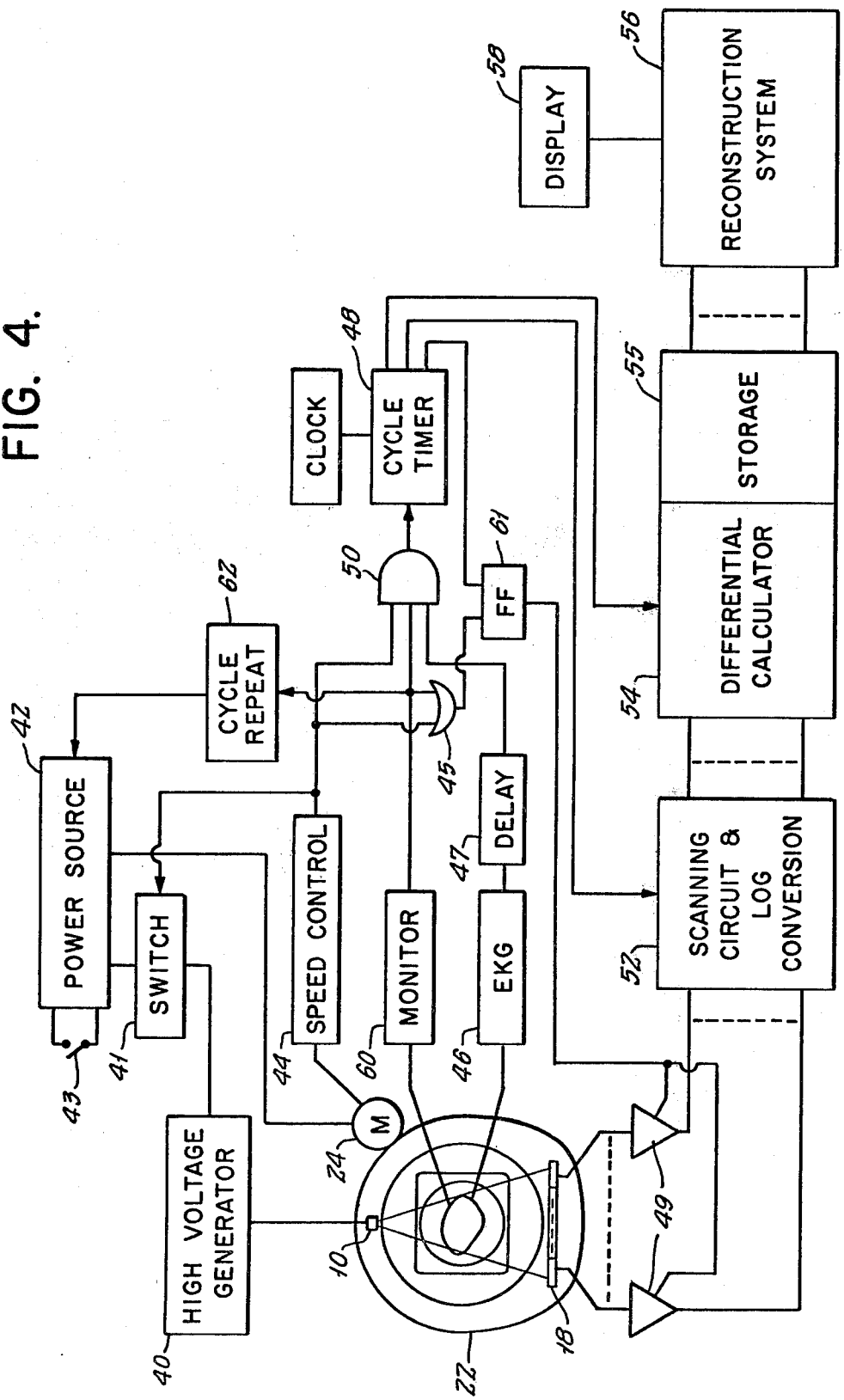
FIG. 4 is a block diagram showing an apparatus employable with the present invention.

Referring now to FIG. 4, therein is illustrated a simplified block diagram of apparatus which may be employed in conjunction with the present invention. As shown therein, the operating voltage for the source 10 is obtained from a suitable conventional high-voltage generator 40, so that the source 10 will produce radiation when high-voltage is applied thereto. The high-voltage generator is energized from a power source 42, for example, by way of a switch 41. The power source 42 is also employed to directly energize the motor 24 which drives the frame 22. A switch 43 or other conventional control device may be connected to the power source 42, in order to enable initiation of a measurement sequence.

A speed control circuit 44 is provided for providing an output control signal when the speed of the motor 24 is proper for the taking of measurements. The speed control circuit may constitute, for example, a tachometer, having a threshold circuit for providing an output only when the motor speed is at a determined level. The output of the speed control 44 may be employed to control the switch 41, as shown in the drawings, so that energizing potential is applied to the high-voltage generator only when the frame 22 is driven at the desired speed for making measurements.

It will be recalled that the measurement cycles are controlled in response to the heartbeat. Thus, a conventional EKG 46 may be connected to the patient, with the output thereof suitably delayed as discussed in a delay circuit 47 of conventional nature, in order to enable the start of a measurement cycle a determined time, such as 3 milliseconds, following the termination of a QRS complex.

The cycle initiation signal output from the delay circuit 47 is applied to a cycle timer 48, for example, by way of an AND gate 50, in order that the operating cycle be initiated in the timer 48. The output of the speed control 44 may also be applied to the AND gate 50, so that a measurement cycle will not commence when the speed of drive of the frame 22 is not proper. In addition, a monitor 60 may also be connected to an input of the AND gate 50, so that a measurement cycle can not be initiated by the EKG 46 in the event of movement of the sample. This latter feature will be discussed in greater detail in the following paragraphs.

The output of the detectors in the detector unit 18 may be simply applied, for example, by way of gated amplifiers 49, to the inputs of a scanning circuit and log conversion circuits 52. This circuit scans the outputs of the amplifiers 49, under the control of scanning pulses sequentially obtained from the cycle timer 48, to produce a sequence of outputs corresponding to the different detectors. The circuit 52 may include suitable ratio circuitry and logarithmic conversion circuitry, such as logarithmic amplifiers, so that the outputs of the circuit 52 are of the form $B = \log Ie/Io$. This value represents the line integral of the values of attenuation data measurable along each beam line. These outputs are applied to a differential calculator 54 which, as above discussed, may comprise subtraction circuits for subtracting signals of the different time slots, thereby forming the difference between values of line integrals. If desired, the control of the subtraction may be effected sequentially, by way of a further sequence output from the cycle timer 48. These differential calculations are stored in a storage unit 55 of the differential calculator, for later use in the reconstruction of the data for display.

In the operation of the system so far described, it is apparent that a measurement cycle will commence when the motor 24 has reached the proper speed, and the EKG 46 has detected a heartbeat. This will cause the cycle timer 48 to effect the scanning of the outputs of the detectors, in the circuit 52. The outputs of the circuit 52 are then differentiated in the circuit 54 and stored. It will be further apparent that the averaging discussed above of the ten measurements taken in each time slot from each detector may also be effected in the scanning circuit 52, by conventional means.

The calculated differentials are stored in the storage circuit 35 until completion of a scan, and then, in reconstruction unit 56 they are given properly weighted absorption values in accordance with standard techniques, such as described, for example, in U.S. Pat. No. 3,778,614, the disclosure of which is incorporated by reference, or in the aforementioned copending and accompanying applications, disclosures of which have been incorporated by reference. By way of example, the foregoing technique can be achieved by utilization of a general purpose computer of the type incorporated in the Tomoscan ® 200, available from Philips Medical Systems, Inc. of Shelton, Conn. In such a case, the programs employed utilize the stored differential absorption values and perform conventional convolutional and back projection programs to provide the properly weighted differentials. The computer can then utilize the properly weighted differentials in a display program for correlating these values into a single composite image representing the differential movements of the object 26 within the field of the beam. The information thus derived is then displayed in an appropriate conventional display device 58.

The monitor device 60, as above discussed, provides an output responsive to gross movement of the object 26. For example, the monitor 60 may comprise optical means for detecting such movement, or means for physically measuring any movement of the object. Since gross movement of the object may result in inaccurate data, as above discussed, the output of the monitor unit 60 is employed to inhibit the initiation of measurement cycles. Absorption data received during a measurement cycle following the initiation of a cycle during which motion commenced will also be meaningless, and for this purpose the output of the monitor 60 may also be employed to control the gated amplifiers 49, so that data is not scanned for the remainder of that cycle. For this purpose, the output of the monitor 60 may be employed to set a bistable device 61, the output of the device 61 serving to control the amplifiers 49. In the event that motion has ceased by the end of the cycle, the bistable device may be reset by the cycle timer 48 so that meaningful data may be taken following the next output of the EKG 46. This type of control may also be provided in the event that the speed of the motor 24 deviates from its desired value, in which case the data will also be meaningless. For this purpose, the output of the speed control 44 may alternatively be employed to set the bistable device 61. An OR gate 45 may be provided for applying the outputs of the speed control device 44 and the monitor 60 to the bistable circuit 61.

As a consequence, differential data is not stored in the store 55 corresponding to any data received when the speed of rotation of the system is improper, or when motion is indicated by the monitor 60. If it should occur that insufficient data is received by the scanner 52 due to excessive movement of the sample in a single revolution of the source 10, it is possible to provide a cycle control which will cause the source to repeat its movement in order to recapture the data lost as a result of the excessive organ displacement. This may be effected, for example, by providing a cycle repeat circuit 62 responsive to excessive duration of periods of motion detected by the monitor 60, in order to reinitiate an entire revolution cycle for the ring 22 by the power source 42. For example, the cycle repeat circuit 62 may merely duplicate the action of the cycle initiation switch 43. Referring to FIGS. 4 and 5, a wave form illustrating the nature of this operation is graphically presented. This, along axis A of FIG. 5 a typical heart movement is shown. During the time represented by the area M, the monitoring device 60 indicates that the organ has moved sufficiently so that the level of sensed data activity has dropped below an acceptable level, indicated generally and symbolically as L. During this time absorption data is irrelevant and the presence of the movement signal indicated along axis B of FIG. 5 causes a shut-off of the flow of data to the scanner, or to storage or to differential calculation, as was described above. By setting a predetermined time limit to the duration of M, cycle control signals shown along axis C may be provided. Cycle control 62 response to the cycle control signal S, shown on axis C of FIG. 5, for reinitiating, through the cycle control 62, a repeat of the entire data processing cycle. The signal M or discontinuous movement signal M, actuates the counter-mechanism in the cycle control which in turned on during the period of time that the M signal is on, either continuously or discontinuously. When the counter reaches an appropriate predetermined level, the signal S is generated and the cycle repeated. It may be possible to build in several cycle repeats into the mechanism using the foregoing technique.

The foregoing technique may be employed in systems utilizing conventional computerized axial tomographic diagnostics, in conjunction with commercially available equipment, as well as by the Tomoscan ® 200 noted above, with computer controlled scanning of attenuation data around a field of interest. To adapt such systems it is necessary only to instruct the computer on the storage of time displaced attenuation signals along an entire path without regard to the calculation of individual element attenuations along that path. A computer may also be programmed to calculate differentials between adjacent paths during a single repetitive motion cycle, store the differentials in appropriate locations indicating the angular position and time of such attenuation data reading, and then reconstruct a composite image over a series of cycles representing the differential points observed. Similarly, using the monitor, an interrupt can be programmed for taking gross movement into account.

It will thus be evident that the foregoing tecnique permits observation of the relative movement per unit time of a boundary layer between two masses of different radiation attenuation characteristics. In addition, where the area of interest is in itself subject to gross movement, the techniques of the present invention may be adapted to compensate for such movement without the loss of significant amounts of data over the normal gross movement motion cycle of an object such as a human heart.

It should be noted that in conventional scanning over a total body plane section, the angular interval must be sufficiently small, conventionally about one-third degree, so as to avoid generation of image reconstruction artifacts in the attenuation coefficients. In the partial scanning technique of the aforesaid copending applications, a smaller area is fully scanned relative to the full body plane. Thus, the angular intervals may be increased, and for objects of heart size, the present invention employs the one degree angular interval.

We claim:

1. An apparatus for tomographically reconstructing differential values of data at points in a plane from input data values which correspond to the values of a plurality of measurable line integrals of said data values, the improvement comprising:
    means for determining the value of each of said line integrals at least two distinct times;
    means for forming the difference between said values of each of said line integrals at two of said times for applying said differences as said data input values, and tomographically reconstructing said differential values, whereby said reconstructed values at said data points correspond to time differentials of the actual data values at said points.

2. The apparatus of claim 1 further comprising means for displaying the said reconstructed values as gray scale values at display points which correspond to said points in a plane.

3. A method for displaying the motion of one mass relative to a second mass along their common boundary, comprising determining the direction and values of the velocity of a plurality of individual differential points along said boundary with respect to successive relative boundary positions, then assigning values to point on a line gray scale corresponding to said direction and values, and displaying said points.

4. Apparatus for displaying the motion of a boundary between two regions which are characterized by different values of a measurable quantity, comprising:

means for measuring the value of said quantity at each of a plurality of measured points at a first time and at a second time;

means for subtracting the value at said second time from the value at said first time, for each of said measured points, to produce differential values representative of each of said measured points; and means for displaying said differential values as gray scale values at display points corresponding to said measured points.

5. A method for displaying the motion of the change in relative positions between two distinguishable regions of an object along the common boundary of said regions, comprising the steps of:

measuring the value of a radiation characteristic along each of a plurality of paths through said object at least two separate points in time;

for each of said paths, determining the signed difference value by taking the difference between said measured values at separate points in time;

reconstructing a difference image by utilizing said difference values as input data values for a computerized transverse tomography reconstruction computation; and displaying said difference image as gray scale values at corresponding image points, whereby the brightness of said displayed points correspond to the signed values of the velocity of said boundary.

6. A method of examining relative movement of two masses of different radiation attenuation characteristics, having a common boundary and moving relative to one another over a repetitive motion cycle, comprising the steps of scanning said masses from a plurality of successive angles about a common center of rotation by directing a beam of radiation over each motion cycle from each of said angles to derive a plurality of attenuation points encompassing the entire motion cycle, calculating a plurality of differential points between adjacent scans of a single motion cycle, and reconstructing a single composite image of all of said differential points for each individual time period of each motion cycle.

7. An apparatus for examining by penetrating radiation a planar cross-section of an object including two masses of different radiation attenuation characteristics, having a common boundary and moving relative to one another over a repetitive motion cycle, comprising a source of radiation and a detection means located in opposition to said source and each adapted to orbit an area under examination so as to examine said object along a plurality of paths from a corresponding plurality of different angles, means for directing said radiation through said two masses from each of said angles over said plurality of paths, means for storing the relative attenuation of radiation along each of said paths, means for calculating differential values from the difference, over the scan interval, of the radiation attenuations between adjacent paths for each of said angles, means for storing all of said differential values, and means for reconstructing a composite image of said differential values for one single motion cycle for each of said angular positions.

8. The method of examination by penetrating radiation of a planar cross-section of two masses each having different radiation attenuation characteristics, having a common boundary and moving relative to one another over a repetitive motion cycle, comprising the steps of:

beginning at a first point of said repetitive motion cycle, detecting the average attenuation of the entire planar cross-section of area to be examined along a first angular position relative to said area over said entire repetitive motion cycle, by sequentially detecting the attenuation over a plurality of equal time intervals of a plurality of segments of said area;

generating a series of differential signals representing the change in average attenuation of adjacent segments within said area per unit of time representing time from one of said time intervals to the next of said time intervals, over the entire repetitive motion cycle;

repeating said detecting and generating steps, beginning each time at the same first point in successive ones of cycles in said repetitive motion cycles, from each of a plurality of further angular positions, thereby generating a plurality of further corresponding differential signals representative of attenuation changes per unit of time from each of said plurality of further angular positions through the area being examined; and correlating said plurality of differential signals into corresponding time locations over one composite cycle of said total number of examined repetitive motion cycles, said correlation providing a set of differential signals for each time position in said repetitive motion cycle, thereby indicating the rate and direction of relative motion of said masses to each other during said motion cycle.

9. A method of examining relative movement of two masses, each having different radiation attenuation characteristics and sharing a common boundary and moving relative to one another over a repetitive motion cycle, comprising the steps of examining the steps of examining said masses within a field of radiation from a plurality of successive angles about a common center of rotation defining said field of radiation, scanning said object over each motion cycle from each of said angles to derive a plurality of attenuation points encompassing the entire motion cycle, calculating a plurality of differential points between adjacent scans of a single motion cycle, reconstructing a single composite image of all of said differential points for each individual time period of each motion cycle, monitoring said boundary position and sensing when said position moves out of said field of said radiation sufficient to render attenuation data irrelevant, and interrupting said calculating step for as long as said position is out of said field.

10. An apparatus for examining by penetrating radiation a planar cross-section of two masses of different radiation attenuation characteristics having a common boundary and moving relative to one another over a repetitive motion cycle, comprising a source of radiation and a detection means located in opposition and adapted to orbit an area under examination so as to examine said object from a plurality of different angles within a defined field of radiation, means for scanning said object by directing a beam of radiation along each of said angles over a plurality of paths, means for storing the relative attenuation of said radiation along each of said paths, means for calculating the difference, over the scan interval, of the attenuations between adjacent paths for each of said angles, means for storing all of said differentials until the completion of one revolution of said orbit, means for reconstructing a composite image of said differential points for one single motion cycle for each of said angular positions, means for monitoring said boundary position and sensing when said position moves out of said field of said radiation sufficient to render attenuation data irrelevant, and means for interrupting said means for said calculating for as long as said position is out of said field.

11. The apparatus of claim 10, further comprising means for monitoring the beginning of each of said repetitive motion cycles, bistable means responsive to the output of said monitoring means for inhibiting the flow data to said means for calculating in response to the detection by said monitor of a movement outside the preset limit of said monitor, a cycle timing device, said cycle timing device automatically resetting said bistable means at the end of each cycle defining a repetition of said repetitive motion if said monitoring means is not activated by movement exceeding a predetermined limit, and means responsive to the quantity of data received by said means for calculating for initiating a repeat of the entire sampling operation in order to recapture data lost as a result of excessive object displacement.

12. The apparatus of claim 11, further comprising means for monitoring the rotational speed of the orbit of said radiation source and detection means, said bistable device further responding to an indication of improper speed from said means for monitoring said speed for inhibiting said means for calculating.

* * * * *

UNITED STATES PATENT AND TRADEMARK OFFICE
CERTIFICATE OF CORRECTION

PATENT NO. : 4,339,799
DATED : July 13, 1982
INVENTOR(S) : Manlio G. Abele, Norman E. Chase, Gareth M. Mair It is certified that error appears in the above—identified patent and that said Letters Patent is hereby corrected as shown below:

Column 10, line 23, delete ""1"" and insert -- $\ell$ --.

Column 13, line 60, delete "in" and insert --is--.

Column 14, line 55, delete "the".

Signed and Sealed this

Twenty-third Day of August 1983

[SEAL]

Attest:

GERALD J. MOSSINGHOFF

Attesting Officer

Commissioner of Patents and Trademarks